United States Patent [19]

Yamada et al.

[11] Patent Number: 5,194,655
[45] Date of Patent: Mar. 16, 1993

[54] POLYMERIZABLE CARBONATES HAVING ETHYLENIC AND ACETYLENIC FUNCTIONS

[75] Inventors: Mitsuo Yamada, Osaka; Kei Aoki, Nara; Satoshi Urano; Ryuzo Mizuguchi, both of Kyoto, all of Japan

[73] Assignee: Nippon Paint Company, Limited, Osaka, Japan

[21] Appl. No.: 699,376

[22] Filed: May 14, 1991

[30] Foreign Application Priority Data

May 17, 1990 [JP] Japan .................................. 2-127784

[51] Int. Cl.$^5$ .............................................. C07C 69/96
[52] U.S. Cl. ........................................ 558/276; 558/260
[58] Field of Search ............................... 558/276, 260

[56] References Cited

U.S. PATENT DOCUMENTS 3,348,939 10/1967 Gier ..................................... 558/260

FOREIGN PATENT DOCUMENTS 0045440 9/1979 Japan ................................. 558/276

OTHER PUBLICATIONS

94(12): 85076t (Berlin et al.).

*Primary Examiner*—Jose G. Dees
*Assistant Examiner*—Barbara S. Frazier
*Attorney, Agent, or Firm*—Millen, White, Zelano and Branigan

[57] ABSTRACT

A carbonate compound having ethylenically unsaturated and acetylenically unsaturated functions are disclosed. The compound is represented by the formula:

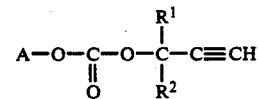

wherein, A is the residue of a hydroxy group-containing, ethylenically unsaturated monomer with removal of the hydroxyl group, $R^1$ and $R^2$ are independently a hydrogen atom or a $C_1$-$C_{20}$ alkyl.

9 Claims, No Drawings

POLYMERIZABLE CARBONATES HAVING ETHYLENIC AND ACETYLENIC FUNCTIONS

BACKGROUND OF THE INVENTION

This invention relates to novel carbonate compounds having ethylenic and acetylenic functions.

It has been known that those compounds having both ethylenic and acetylenic functions may be polymerized to produce polydiacetylene polymers useful as electroconductive materials, nonlinear optical materials and thermochromism materials. Examples of such monomers and polymers are propargyl acrylate, propargyl methacrylate and their polymers reported by Kato et al., in *Kobunshi Ronbunshu*, Vol. 46, No. 5,313 (1989). These known monomers include a carboxylate linkage to couple the ethylenic and acetylenic functions together in a single molecule.

SUMMARY OF THE INVENTION

According to the present invention, a novel compound is provided in which the ethylenic and acetylenic functions are coupled together by a heat-stable carbonate linkage.

The present invention provides a compound of the formula:

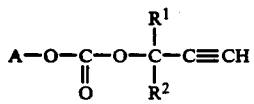

wherein, A is the residue of a hydroxyl group-containing ethylenically unsaturated monomer with removal of the hydroxyl group, $R^1$ and $R^2$ re independently a hydrogen atom or a $C_1$-$C_{20}$ alkyl.

The compound of this invention may be synthesized by reacting a hydroxyl group-containing monomer of the formula: A—OH with a chloroformate of the formula:

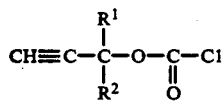

wherein A, $R^1$ and $R^2$ are as defined, in the presence of an acid acceptor, or alternatively by reacting a chloroformate of the formula:

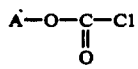

with an alcohol of the formula:

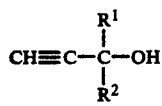

wherein A, R1 and R2 are as defined, in the presence of an acid acceptor.

DETAILED DISCUSSION

The compounds of this invention may be produced, according to the known method, starting from a hydroxyl group-containing, ethylenically unsaturated monomer and an acetylenic alcohol such as propargyl alcohol.

Hydroxyl group-containing, ethylenically unsaturated monomers include ethylenically unsaturated alcohols, hydroxyl group-containing acrylate and methacrylates (hereinafter collectively referred to as "(meth)acrylate"), hydroxyl group-containing (meth)acrylamides, and hydroxyl group-containing styrene derivatives.

Specific examples of these monomers are as follows:

Ethylenically Unsaturated Alcohols

Allyl alcohol.

Hydroxyl Group-containing (Meth)Acrylates

2-Hydroxyethyl (meth)acrylate,
2-hydroxypropyl (meth)acrylate,
2-hydroxybutyl (meth)acrylate,
2-hydroxycyclohexyl (meth)acrylate,
2-(2-hydroxyethoxy)ethyl (meth)acrylate,
2-(2-hydroxy-1,1-dimethylethoxy)-1,1-dimethylethyl (meth)acrylate,
2-hydroxy-2-phenylethyl (meth)acrylate,
2-hydroxy-3-phenoxypropyl (meth)acrylate,
2-hydroxy-3-(2-propenyloxy)propyl, (meth)acrylate
2-hydroxy-3-propoxypropyl (meth)acrylate,
2-hydroxy-3-butoxypropyl (meth)acrylate,
4-benzoyl-3-hydroxyphenyl (meth)acrylate,
2-hydroxy-3-sulfopropyl (meth)acrylate,
2-hydroxy-3-piperidinopropyl (meth)acrylate,
2-hydroxy-3-(N-methyl-N-2-hydroxyethylamino)propyl (meth)acrylate,
mono(meth)acrylate esters of polyether diols such as polyethylene glycol, polypropylene glycol or polytetramethylene glycol, and
mono(meth)acrylate esters of polyester diols such as poly-ε-caprolactone.

Hydroxylgroup-Containing (Meth)Acrylamide Derivatives

N-(2-Hydroxyethyl)acrylamide,
N-(2-hydroxypropyl)acrylamide,
N-(1,1-dimethyl-2-hydroxyethyl)acrylamide,
N-(1-ethyl-2-hydroxyethyl)acrylamide,
N-(1,1-dimethyl-3-hydroxybutyl)acrylamide,
N-(2-hydroxyethyl)-N-methylacrylamide,
N-(2,2,2-trichloro-1-hydroxyethyl)acrylamide,
N-(2,2,2-trichloro-1-hydroxypropyl)acrylamide, and corresponding methacrylamide derivatives.

Hydroxyl Group-Containing Styrene Derivatives

4-Vinylphenol,
methyl 4-vinylsalicylate,
methyl 3-vinylsalicylate,
methyl 5-vinylsalicylate,
4-methoxy-2-hydroxy-4'-vinylbenzophenone,
4-ethoxy-2-hydroxy-4'-vinylbenzophenone, and
4-n-butoxy-2-hydroxy-4'-vinylbenzophenone.

Acetylenic alcohols used in the synthesis of the carbonate compounds of this invention include propargyl alcohol and its α-mono- and α, α-di-$C_1$-$C_{20}$ alkyl derivatives. Propargyl alcohol is preferred.

The carbonate compounds of this invention may be synthesized by reacting either one of the hydroxyl group-containing, ethylenically unsaturated monomer and the acetylenic alcohol with prosgene to form the corresponding chloroformate followed by reacting the latter with the other. The reaction of the chloroformate of acetylenic alcohol with the hydroxyl group-containing monomer is preferred.

The reaction may be performed, as is conventional, in an inert solvent in the presence of an acid acceptor.

Examples of usable inert solvents include DMSO, DMF, N-methylpyrrolidone, acetone, methyl ethyl ketone, methyl isobutyl ketone, benzene, toluene, xylene, diethyl ether, tetrahydrofuran, dioxane, methylene chloride, dichloroethane and the like. When the reaction system is not too viscous, the reaction may be performed without using the solvent.

Examples of acid acceptors include trimethylamine, triethylamine, pyridine, sodium hydroxide, potassium hydroxide, calcium hydroxide, magnesium hydroxide, sodium silicate, sodium aluminate, sodium carbonate, potassium carbonate, alkali metal ethoxide and the like. Tertiary amines and pyridine are preferred.

The reaction is preferably carried out under the nitrogen gas atmosphere to prevent coloration of the product. The reaction temperature may range from room temperature to the boiling point of the solvent used.

After the reaction, the product may be isolated by the conventional technique from the reaction mixture and further purified, if desired.

In order to prevent the polymerization of the starting monomer and the reaction product from occurring during the reaction and the purification process, it is often desirable to use a small amount of a polymerization inhibitor such as 2,6-di-t-butyl-4-methylphenol, methylhydroquinone, p-t-butylcatechol, phenothiazone, benzophenothiazine, acetamidophenothiazine, p-benzoquinone, naphthoquinone, N-nitrosodiphenylamine, N-nitrosodimethylamine and the like.

The carbonate compounds thus prepared may be polymerized with a metallic catalyst or initiator, or by irradiating with actinic radiations such as UV radiation, gamma radiation of electron beam radiation. They are, therefore, useful as stock materials of resins used in paints, electric and electronic components, structural materials and nonlinear optical materials where nonemanating cure, and durability and heat resistance properties are desired in the finished products.

The invention is illustrated by the following examples wherein all parts and percents are by weight unless otherwise specified.

EXAMPLE 1

2-Propargyloxycarbonyloxyethyl Methacrylate

A flask equipped with a stirrer, thermometer, nitrogen gas tube and reflux condenser was charged with 13.0 g of 2-hydroxyethyl methacrylate and 11.5 g of trimethylamine in 50.0 g of methylene chloride. To the flask was added 13.0 g of propargyl chloroformate dropwise over one hour. The mixture was allowed to react for 6 hours at 30° C. After the reaction, the mixture was treated with methylene chloride-water mixture. The organic phase was separated and dried over magnesium sulfate. After filtering, the filtrate was evaporated in a rotary evaporator. The resulting residue was applied on a 200 mesh silica gel column and developed with ethyl acetate-hexane mixture. The title compound was obtained as colorless liquid. Yield was 73.6% of theory.

Its structure was identified by the IR spectrum and $^1$H—NMR.

IR (cm$^{-1}$) 3300, 2110, 2950, 1750, 1720, 1630

$^1$H—NMR (δ, CDCl$_3$) 1.95 (—CH$_3$), 2.53 (CH≡C—), 4.39 (—CH$_2$—), 4.78 (≡C—CH$_2$—), 5.58–6.14 (CH$_2$=C—)

EXAMPLE 2

2-Propargyloxycarbonyloxyethyl Acrylate

Analogous to Example 1, the title compound was produced by reacting 2-hydroxyethyl acrylate with propargyl chloroformate. Yield was 78.5% of theory.

IR (cm$^{-1}$) 3300, 2100, 1760, 1740, 1630

$^1$H—NMR (δ, CDCl$_3$) 2.55 (CH≡C—), 4.40 (—CH$_2$—), 4.78 (≡C—CH$_2$—), 5.80–6.40 (=CH—)

Analogue to Example 1, the following compounds were produced.

EXAMPLE 3

N-(2-Propargyloxycarbonyloxyethyl)Acrylamide yield 88.2%

IR (cm$^{-1}$) 3300, 2100, 1760, 1740, 1670, 1625

$^1$H—NMR (δ, ppm) 2.50 (CH≡C—), 4.1–4.50 (—CH$_2$—), 5.80–6.40 (CH$_2$=CH—)

EXAMPLE 4

N-(2-Propargyloxycarbonyloxyethyl)Methacrylamide yield, 77.6%

IR (cm$^{-1}$) 3300, 2110, 1760, 1740, 1680, 1620

$^1$H—NMR (δ, ppm) 1.91 (—CH$_3$), 2.48 (CH≡C—), 4.1–4.50 (—CH$_2$—), 4.76 (≡C—CH$_2$—), 5.80–6.40

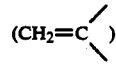

EXAMPLE 5

3-(1,1-Dimethyl-2-Propinyl)oxycarbonyloxypropyl Methacrylate yield, 82.5%

IR (cm$^{-1}$) 3300, 2100, 1760, 1740, 1630 $^1$H—NMR (δ, ppm) 1.95 (—CH$_3$), 2.53 (CH≡C—), 4.39 (—CH$_2$—), 4.78 (≡C—CH$_2$—) 5.58–6.14

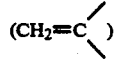

EXAMPLE 6

4-Propargyloxycarbonyloxystyrene yield, 77.2%

IR (cm$^{-1}$) 3300, 2100, 1750, 1630, 1600, 1500

$^1$H—NMR (δ, ppm) 2.53 (CH≡C—), 4.39 (—CH$_2$—), 4.78 (≡C—CH$_2$—), 5.58–6.14 (CH$_2$=C—)

EXAMPLE 7

Carbonate of Propargyl Alcohol and 2-Hydroxyethyl Methacrylate-Polycaprolactone Adduct of the Formula:

$$CH_2=C(CH_3)-C(=O)-OCH_2CH_2-(OCCH_2CH_2CH_2CH_2CH_2)_5-O-C(=O)-OCH_2C\equiv CH$$

Yield, 66.3%
IR (cm$^{-1}$) 3300, 2100, 1760, 1740, 1630
$^1$H—NMR (δ, ppm) 1.95 (—CH$_3$), 2.53 (CH≡C—), 4.39 (—CH$_2$—), 4.78 (≡C—CH$_2$—), 5.58–6.14 (CH$_2$=C—)

EXAMPLE 8

Carbonate of Propargyl Alcohol and Penta(Tetramethyleneglycol) of the Formula:

$$CH_2=C(CH_3)-C(=O)-(OCH_2CH_2CH_2CH_2)_5-O-C(=O)-OCH_2C\equiv CH$$

Yield, 67.8%
IR (cm$^{-1}$) 3300, 2100, 1760, 1740, 1630, 1100
$^1$H—NMR (δ, ppm) 2.53 (CH≡C—), 4.78 (≡C—CH$_2$—), 5.58–6.14 (CH$_2$=C—)

EXAMPLE 9

N-(3-Methacryloyloxy-2-Hydroxypropyl)-N-Methyl-N-(2-Propargyloxycarbonyloxyethyl)Amine yield, 73.6%
IR (cm$^{-1}$) 3400, 3300, 2110, 1760, 1740, 1630
$^1$H—NMR (δ, ppm) 2.53 (CH≡C—), 4.78 (≡C—CH$_2$—), 5.58–6.14 (CH$_2$=C—)

EXAMPLE 10

2-Hydroxy-1-Propargyloxycarbonyloxy-3-Vinyloxy-propane yield, 77.2%
IR (cm$^{-1}$) 3300, 2100, 2950, 1750, 1720, 1630
$^1$H—NMR (δ, ppm) 1.95 (—CH$_3$), 2.53 (CH≡C—), 4.39 (—CH$_2$—), 5.58–6.14 (CH$_2$=C—)

EXAMPLE 11

A flask use in Example 1 was charged with 19.3 g of 2-methacryloyloxyethyl chloroformate and 11.5 g of trimethylamine in 50.0 g of methylene chloride. To the flask was added 7.0 g of propargyl alcohol dropwise over one hour. The mixture was allowed to react for 6 hours at 30° C. After the reaction, the mixture was processed as in Example 1 to give 2-propargyloxycarbonyloxyethyl methacrylate as colorless liquid. Yield, 53.6% of theory. The product was identified to be the same as the product of Example 1 by the IR spectrum and $^1$H—NMR.

What is claimed is:

1. A carbonate compound of the formula:

$$A-O-C(=O)-O-C(R^1)(R^2)-C\equiv CH$$

wherein A is the residue of a hydroxyl group-containing ethylenically unsaturated monomer selected from a group consisting of, hydroxyl group-containing acrylates and hydroxyl group-containing methacrylates, and R$^1$ and R$^2$ are independently a hydrogen atom or C$_1$–C$_{20}$ alkyl.

2. The carbonate compound as claimed in claim 1, wherein R$^1$ and R$^2$ are both hydrogen atoms.
3. The carbonate compound as claimed in claim 2, wherein said residue is acryloyloxyalkyl.
4. The carbonate compound as claimed in claim 2, wherein said residue is methacryloyloxyalkyl.
5. The carbonate compound as claimed in claim 3, which is 2-propargyloxycarbonyloxyethyl acrylate.
6. The carbonate compound as claimed in claim 4, which is 2-propargyloxycarbonyloxyethyl methacrylate.
7. 3-(1,1-dimethyl-2-propinyl)oxycarbonyloxy-propyl methacrylate, a compound of claim 1.
8. The methacrylate-polycaprolactone adduct of claim 1 of the formula:

$$CH_2=C(CH_3)-C(=O)-OCH_2CH_2-(OCCH_2CH_2CH_2CH_2CH_2)_5-O-C(=O)-OCH_2C\equiv CH.$$

9. The carbonate of propargyl alcohol and penta(tetramethyleneglycol) of claim 1 of the formula:

$$CH_2=C(CH_3)-C(=O)-(OCH_2CH_2CH_2CH_2)_5-O-C(=O)-OCH_2C\equiv CH.$$

* * * * *